United States Patent [19]
Constantz et al.

[11] Patent Number: 5,231,169
[45] Date of Patent: Jul. 27, 1993

[54] MINERALIZED COLLAGEN

[75] Inventors: Brent R. Constantz, Scotts Valley; Subramanian Gunasekaran, Newark, both of Calif.

[73] Assignee: Norian Corporation, Mountain View, Calif.

[21] Appl. No.: 842,788

[22] Filed: Feb. 26, 1992

Related U.S. Application Data

[63] Continuation of Ser. No. 599,000, Oct. 17, 1990, abandoned.

[51] Int. Cl.⁵ .................... A61K 37/12; C07K 15/20; C08H 1/06; C08L 89/00
[52] U.S. Cl. .................... 530/356; 106/35; 106/124; 106/645; 106/691; 128/DIG. 8; 424/423
[58] Field of Search .................... 514/21, 801, 953; 424/423, 484; 128/DIG. 8; 606/76; 623/16; 106/124, 155, 35, 691, 645; 501/1; 530/356; 423/308, 309, 311

[56] References Cited

U.S. PATENT DOCUMENTS

| | | | |
|---|---|---|---|
| 3,443,261 | 5/1969 | Battista et al. | 106/155 |
| 3,968,567 | 7/1976 | Nevins | 623/66 |
| 4,172,128 | 10/1979 | Thiele et al. | 433/173 |
| 4,780,450 | 10/1988 | Sauk et al. | 623/16 |
| 4,795,467 | 1/1989 | Piez et al. | 623/16 |
| 4,880,610 | 11/1989 | Constantz | 623/16 |

OTHER PUBLICATIONS

Glimcher, *Phil. Trans. R. Soc. Long. B.* 304, 479–508 (1984).
Lowenstam and Weiner, *On Biomineralization*, (1988), pp. 149–158.

*Primary Examiner*—Jeffrey E. Russel
*Attorney, Agent, or Firm*—Bertram I. Rowland

[57] ABSTRACT

Mineralized collagen is prepared by forming calcium phosphate mineral under mild agitation in situ in the presence of dispersed collagen fibrils. A stable composition is obtained with desirable physical characteristics mimicking the characteristics of bone.

12 Claims, No Drawings

MINERALIZED COLLAGEN

This is a continuation of application Ser. No. 07/599,000, filed Oct. 17, 1990, now abandoned.

TECHNICAL FIELD

The field of this invention is mineralized collagen.

BACKGROUND

Enhancement of the compressive, tensile, flexural and fatigue properties of organic composites, has and continues to be an elusive goal. Since the utilization of organic composites in high performance applications is ever-increasing, so is the need to enhance mechanical behavior of these widely used materials.

By mimicking cell-assembled biological materials with high compressive strengths, similar attractive properties may be engineered into new synthetic composites. Bone is a biological composite with an average modulus of elasticity of about 20 $GN/m^2$, compressive strength of 170-220 $MN/m^2$, tensile strength of 180 $MN/m^2$ and bending strength of 220-270 $MN/m^2$.

Bone differs from other composite materials in that it possesses an orderly intimate combination of a calcium phosphate mineral phase within the collagen biopolymer matrix phase. The calcium phosphate appears to be assembled at gaps in the collagen fibrils to create mineral-polymer composite fibers. These mineralized collagen fibers are bonded together in an orderly manner by further calcium phosphate cementation, producing a self-assembling composite.

Bone is characteristically composed of type I collagen fibrils intimately associated in an orderly manner with calcium phosphate crystals. Minor constituents include an array of macromolecules as well as a series of small molecules associated mainly with the mineral phase. Besides bone, similar composite structures are also found in tooth dentin and cementum, fish scales and mineralized tendons. Although the ultrastructural organizational patterns of these tissues differ from one another and from most bones, they all appear to have many properties in common at the molecular level of organization. For example, during their formation collagen is synthesized, extruded from the cell to form self-assembled fibrils in the extracellular space before mineralization begins.

One feature of bone is the exceedingly small size of the crystals. Bone crystals are certainly among the smallest biologically formed crystals known and, in fact, most crystallographers would intuitively not expect crystals just a few unit cells thick to be stable at all. Therefore, the collagen bone structure has unique characteristics as to its formation, components, and properties.

Since collagen is readily available from a wide variety of natural sources and by mineralizing collagen, unique properties may be achievable, there is substantial interest in providing for methods for producing mineralized collagen having characteristics useful for applications in the biomedical as well as other fields.

RELEVANT LITERATURE

The protein composition of bone is described by Delmas et al., *Calcif. Tissue Int.* 3636:308-316 (1984); Tracy et al. *In: Development and Diseases of Cartilage and Bone Matrix.* ed. A. Sen and T. Thornhill, Alan R. Liss, N.Y. 127-136, (1987). Glimcher, Phil., *Trans. R. Soc. Lond.* B304 479-508 (1984) describes mineral phases in bone. See also, *Calcified Tissue,* ed. David W. L. Hukinz, CRC Press Ins., Boca Raton, Fl., 1989, chapters 6 and 7.

SUMMARY OF THE INVENTION

Mineralized collagen is achieved by employing dispersed or solubilized collagen in a basic pH medium and preparing calcium phosphate in situ. The resulting product has calcium phosphate stably dispersed in an ordered manner associated with the collagen fibrils.

DESCRIPTION OF THE SPECIFIC EMBODIMENTS

Methods and compositions are provided relating to mineralized collagen, where the product has a substantially uniform distribution of calcium phosphate crystals distributed through collagen fibrils. The method employs preparing calcium phosphate in situ in a dispersion of collagen fibrils at high pH. The calcium phosphate is formed in situ by the simultaneous gradual addition, preferably continuous addition, of a source of soluble calcium and a source of soluble phosphate to the collagen-fibril-containing medium. Other components which are to be incorporated into the crystal lattice will also be present. The resulting product after thorough washing in distilled water has calcium phosphate stably distributed with the fibrils to form a substantially uniform composition of calcium phosphate and collagen. The mineral phase will usually have a Ca:P ratio of 1.2-1.8, hexagonal symmetry and be a member of the hydroxyapatite mineral group.

The collagen may come from mineralized or unmineralized collagen sources, usually unmineralized collagen sources. Thus, the collagen may come from bone, tendons, skin, or the like, preferably collagen which involves a combination of two strands of $\alpha_2$ collagen chains. The collagen may be from a young source, e.g., calf, or a mature source, e.g., cow of 2 or more years. The particular source of the collagen, may be any convenient animal source, mammalian or avian, and may include bovine, porcine, equine, or the like, or chicken, turkey, or other domestic source of collagen. The collagen which is employed will normally be dispersed or solubilized collagen where solubilization is achieved by dispersing the collagen source in a medium at an elevated pH, using at least about pH 8, more usually about pH 11-12, and generally less than about 1 N. Commonly, sodium hydroxide is employed, although other hydroxides may find use, such as other alkali metal hydroxides or ammonium hydroxide.

The concentration of collagen will generally be in the range of about 0.1 to 10 weight percent, more usually from about 1 to 5 weight percent. The collagen medium will generally be at a concentration of the base in the range of about 0.0001 to 0.1 N. The pH is generally maintained during the course of the reaction in the about 10-13, preferably about 12.

The phosphate and calcium are added as solutions, generally at a concentration in the range of about 0.001-0.5 M, preferably about 0.025-0.2 M. The volume of the solutions added to the collagen medium will generally increase the collagen medium volume by at least 10 percent, usually at least 25 percent and not more than about 400 percent, generally in the range of about 50 to 150 percent. Thus, the collagen solution will generally not be diluted by more than four-fold.

Besides a source of calcium and phosphate, sources of other ions may be employed, such as carbonate, chloride, fluoride, sodium or ammonium. The presence of carbonate results in a product having the properties of dahlite (carbonated hydroxyapatite), while fluoride provides a product having the properties of fluoridated apatite. The weight % of carbonate will usually not exceed 10, while the weight % of fluoride will usually not exceed 2, preferably in the range of 0 to 1. These ions may be present in conjunction with the calcium and/or phosphate source, so long as the ions are compatible and do not result in precipitation in the reagent solutions. For the most part, the counter ions will be selected so as to be physiologically acceptable and not interfere with the mineralization of the collagen fibrils. For the most part the counter ions for calcium will be chloride, oxide, hydroxide, various calcium phosphates, and the like. For the most part, the counter ions for the phosphate will be alkali metals or ammonium, particularly sodium.

The rate of addition is relatively slow, generally requiring at least about one hour and not more than about 72 hours, generally being in the range of about 2 to 18 hours, more usually in the range of about 4 to 16 hours. For example, with one liter of a collagen dispersion, where about a total of about one liter of reagents is added, the rate of addition will generally be in the range of 20 to 150 ml per hour.

The addition of the reagents can be provided in a stoichiometric ratio, although stoichiometry is not required, variations from stoichiometry of up to about 50 percent, preferably not more than about 25 percent are preferred. Thus, where the stoichiometry of addition is not maintained, one of the components may be exhausted, while addition of the other components continue.

During the course of the reaction, mild agitation is maintained, so as to ensure substantially uniform mixing of the collagen fibrils and the calcium phosphate mineral. Mild temperatures are employed, usually not less than about 4° C. and not more than about 40° C, preferably in the range of about 15 to 30° C. The weight ratio of the collagen to calcium phosphate mineral will generally be in the range of about 8:2 to 1:1, more usually about 7:3.

The nature of the calcium phosphate mineral may be varied widely, including calcium hydroxyapatite, calcium hydroxy/fluorapatite, brushite, dahlite, monetite, phosphated calcium carbonate (calcite), octacalcium phosphate, tricalcium phosphate, where the choice of stoichiometry of the calcium and the phosphate, as well as the presence of other ions, will result in the particular composition. Thus, by varying the calcium to phosphate ratio, a range of mineral compositions may be attained. Other non-collagenous proteins or factors, such as BMP-2, calcitonin, etc. may be included in the solubilized or dispersed collagen slurry, prior to Ca and $PO_4$ addition. The amount of such additives will generally be in the range of about 0.0001 to 2 weight % based on collagen. The added protein may combine with the mineral as it forms on the collagen, binding the added protein to the collagen.

After completion of the addition, agitation, e.g., stirring, will normally be continued, usually at least about 1 h, more usually about 2 h and agitation may continue even more. The amount of continued agitation is not critical to the preparation of the product.

Upon completion of the reaction, the product may be treated in a variety of ways. The product may be washed repeatedly to remove any unbound minerals or other components of the medium, as well as provide a more neutral pH. may be readily accomplished with water, saline, mild acids or the like. The product may be stored in solution, may be lyophilized, filtered and dried, or the like.

The amount of collagen present in the final product will generally be from about 80% to 30%. The bulk density of the final product will be in the range of about 0.01 to 0.5. The mineralized collagen will retain the calcium phosphate mineral under standard temperature and humidity. The TEM/SEM and FTIR indicate the presence of both collagen and calcium phosphate mineral which is more likely a carbonated apatite.

The subject compositions may be further treated in a variety of ways. The subject compositions may be cross-linked using a variety of cross-linking agents, such as formaldehyde, glutaraldehyde, chromium salts, diisocyanates or the like. The subject compositions may be combined with other compositions, such as hydroxyapatite, as gravel, slurry, powder, etc. These combinations may find use for different hard tissue implantations.

The subject composition may find application in a wide variety of bio-medical uses, by themselves or in combination. The subject composition may be used for the production of prosthetic devices, bone filler, hemostatic agent for bone-bleeding, etc.

The mineralized collagen has application as an osteoconductive bone grafting material for non-union fractures, periodontal defect filler and bony defect filler. By combining the subject composition with an osteoinductive material, such as autologous aspirated bone marrow, bone morphogenic protein, calcitonin or other growth factors, bone induction and growth may be further augmented. The subject compositions find application in soft tissue augmentation, such as urinary sphincter augmentation, dermal wrinkle augmentation and burn tissue repair. In addition, the subject compositions may be used as a hemostatic agent, particularly for hard tissue bleeding.

The following examples are offered by way of illustration and not by way of limitation.

EXPERIMENTAL

Example 1: Reaction solutions were prepared of 0.06M sodium phosphate (tri-basic) and 0.1 M calcium chloride. Bovine tendon collagen (2.15 g) was solubilized in one liter of sodium hydroxide, pH 12. The reagent solutions were added simultaneously over a period of five hours and ten minutes. The mixture was kept in the refrigerator undisturbed overnight. The mineralized collagen product was centrifuged and then washed three times with deionized water followed by centrifugation. (U-0071). The weight ratio of collagen to mineral was 7:3.

The above experiment was repeated except that the collagen source was different. Avian bone collagen from Medimatrix was employed. (U-0074).

The above samples were lyophilized and viewed under SEM (Scanning Electron Microscope). While no banding structure was observed, a fibrillar structure was seen. EDS (Electron Dispersive Spectrometry) showed a similar calcium to phosphorous ratio as seen in hydroxyapatite, with the calcium distributed uniformly throughout the sample. This is evident with the SEM elemental analyses. When a portion of the sample U-0071 which was not lyophilized was suspended in 500 ml of deionized water, and blended for one minute, followed by pouring into a 500 ml graduated cylinder and kept undisturbed in a refrigerator, at four hours no separation of phases was observed.

The lyophilized powders were measured for bulk (apparent) density, where U-0071 was found to be 0.04, while U-0074 was found to be 0.01.

Example 2: Avian bone collagen (11.6 g) was dissolved in 1 liter of dilute NaOH solution (pH 12). Reagent solutions of sodium tri-basic phosphate and calcium chloride at 0.06 M and 0.1 M, respectively were prepared. The concentration of the collagen in the solution was approximately 1% (w/v). The addition of the reagents required 72 hours and provided a ratio of 70% collagen: 30% hydroxyapatite by weight. At the end of this time, the reaction was stopped and the sample stored in a refrigerator. The sample was washed three times in distilled water with centrifugation and then stored in a freezer (U-0084).

The above results demonstrate that one can prepare stable mineralized collagen for a variety of uses. The calcium phosphate mineral is stably distributed in the collagen to provide a product having desirable physical properties and mimicks bone. It is mineralogically, biochemically, and ultrastructurally nearly identical to mineralized bone. Spacial arrangements of crystals of hydroxyapatite and collagen, shield the crystals from being perceived by the immune system as foreign bodies, analogous to the way that ceramic gravels mixed with collagen are used.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of mineralizing collagen with a calcium phosphate mineral, said method comprising:
   preparing said calcium phosphate mineral in the presence of a dispersion of solubilized or dispersed collagen fibrils in basic pH aqueous medium, wherein the amount of collagen present will result in a product having from about 30–80 wt. % of collagen, said pH in the range of about 10–13, by adding over at least one hour to said dispersion a source of soluble calcium and soluble phosphate in the correct ratio sufficient to product said calcium phosphate mineral; and
   collecting the mineralized collagen.

2. A method according to claim 1, wherein said calcium phosphate mineral has a Ca:P ratio of 1.2–1.8, has hexagonal symmetry and is a member of the hydroxyapatite mineral group.

3. A method according to claim 1, wherein said dispersion is a solution.

4. A method according to claim 1, wherein said pH is in the range of 10 to 13 and is maintained during said preparing.

5. A method according to claim 1, wherein said source of calcium is calcium chloride and said source of phosphate is sodium or ammonium phosphate.

6. A method according to claim 1, wherein the addition of said source of calcium and said source of phosphate during said preparing is at other than in stoichiometric proportion.

7. A method according to claim 1, wherein said collagen is bovine collagen.

8. A method according to claim 1, wherein said collagen is avian collagen.

9. A method according to claim 1, wherein a non-collagenous protein moiety is added to said dispersion prior to said adding.

10. A method of mineralizing collagen with a calcium phosphate mineral, said method comprising:
    preparing said calcium phosphate mineral in situ in the presence of a dispersion of solubilized or dispersed collagen fibrils in basic pH aqueous medium at a pH of about 12 by adding calcium chloride and sodium phosphate solutions to said dispersion in the correct stoichiometry for said calcium phosphate mineral over a period of at least one hour, wherein the volume of said dispersion is diluted less than about four-fold, wherein the amount of collagen is about 30 to 80 weight percent of said mineralized collagen;
    isolating the mineralized collagen and washing said mineralized collagen; and
    drying said mineralized collagen.

11. In a method for replacing bone, the improvement which comprises:
    employing a mineralized collagen prepared according to the method of claim 1 in said replacing.

12. A method of mineralizing collagen with a carbonate containing calcium phosphate mineral, said method comprising:
    preparing said carbonate-containing phosphate mineral in the presence of a dispersion of solubilized or dispersed collagen fibrils in basic pH aqueous medium, said pH in the range of about 10–13 by adding over at least one hour to said dispersion a source of soluble calcium, soluble phosphate and carbonate in the correct stoichiometry for said carbonate containing calcium phosphate mineral, wherein said carbonate is present in said mineral in an amount up to 10 wt. % and the amount of collagen present will result in a mineralized collagen having from 30 to 80 wt. % of collagen; and
    collecting the mineralized collagen.

* * * * *